United States Patent
Tanaka et al.

(10) Patent No.: US 8,030,022 B2
(45) Date of Patent: Oct. 4, 2011

(54) MICROORGANISM AND METHOD FOR PRODUCING CAROTENOID USING IT

(75) Inventors: Toru Tanaka, Kawasaki (JP); Teruhiko Ide, Hachioji (JP)

(73) Assignee: Tosoh Corporation, Shunan-shi (JP)

( * ) Notice: Subject to any disclaimer, the term of this patent is extended or adjusted under 35 U.S.C. 154(b) by 535 days.

(21) Appl. No.: 12/095,511

(22) PCT Filed: Oct. 19, 2006

(86) PCT No.: PCT/JP2006/320829
§ 371 (c)(1),
(2), (4) Date: May 30, 2008

(87) PCT Pub. No.: WO2007/066454
PCT Pub. Date: Jun. 14, 2007

(65) Prior Publication Data
US 2010/0285524 A1 Nov. 11, 2010

(30) Foreign Application Priority Data
Dec. 6, 2005 (JP) .................................. 2005-352140

(51) Int. Cl.
C12P 23/00 (2006.01)

(52) U.S. Cl. ........................ 435/67; 435/170; 435/252.1
(58) Field of Classification Search .......................... None
See application file for complete search history.

(56) References Cited

U.S. PATENT DOCUMENTS
5,935,808 A * 8/1999 Hirschberg et al. ............. 435/67

FOREIGN PATENT DOCUMENTS

| | | |
|---|---|---|
| EP | 1 138 208 A1 | 10/2001 |
| EP | 1 229 126 A1 | 8/2002 |
| EP | 1 496 115 | 1/2005 |
| JP | 6 237787 | 8/1994 |
| JP | 9-308481 | 12/1997 |
| JP | 2001 512030 | 8/2001 |
| JP | 2003 304875 | 10/2003 |
| WO | WO 99/06586 | 2/1999 |
| WO | 2005 049643 | 6/2005 |

OTHER PUBLICATIONS

Akihiro Yokoyama, et al., "Composition and Presumed Biosynthetic Pathway of Carotenoids in the Astaxanthin-Producing Bacterium Agrobacterium Aurantiacum", FEMS Microbiology Letters, vol. 128, No. 2, Jan. 1, 1995, XP002206362, pp. 139-144.
Ralley, L., et al., "Metabolic Engineering of Ketocarotenoid Formation in Higher Plants", The Plant Journal, vol. 39, pp. 477 to 486, 2004.
Linden, Hartmut, "Carotenoid Hydroxylase From *Haematococcus pluvialis*: cDNA Sequence, Regulation and Functional Complementation", Biochimica et Biophysica Acta, vol. 1446, pp. 203 to 212, 1999.
Johnson, Eric A., et al., "Microbial Carotenoids", Advances in Biochemical Engineering Biotechnology, vol. 53, pp. 119 to 178, 1995.
Yokoyama, Akihiro et al., "Production of Astaxanthin and 4-Ketozeaxanthin by the Marine Bacterium, Agro-bacterium aurantiacum", Biosci. Biotech. Biochem., vol. 58, No. 10, pp. 1842 to 1844, 1994.
Norihiko, Misawa et al., "Structure and Functional Analysis of a Marine Bacterial Carotenoid Biosynthesis Gene Cluster and Astaxanthin Biosynthetic Pathway Proposed at the Gene Level"Journal of Bacteriology, vol. 177, No. 22, pp. 6575 to 6584, 1995.
Pasamontes, Luis et al., "Isolation and Characterization of the Carotenoid Biosynthesis Genes of *Flavobacterium* sp. Strain R1534", Gene, vol. 185, pp. 35 to 41, 1997.
European Third Party Observation issued Jan. 4, 2011, in Patent Application No. 06821955.9.
Akira Tsubokura et al., " *Paracoccus carotinifaciens* sp. nov., a new aerobic Gram-negative astaxanthin-producing bacterium", International Journal of Systematic Bacteriology, vol. 49, 1999, pp. 277-282.

* cited by examiner

*Primary Examiner* — Kade Ariani
(74) *Attorney, Agent, or Firm* — Oblon, Spivak, McClelland, Maier & Neustadt, L.L.P.

(57) ABSTRACT

A carotenoid producing bacterium belonging to the genus *Paracoccus* that selectively produces canthaxanthin so that the amount thereof is not less than 90 percent by weight of the total amount of produced carotenoids including β-carotene, β-cryptoxanthin, echinenone, canthaxanthin, 3-hydroxyechinenone, 3'-hydroxyechinenone, zeaxanthin, phoenicoxanthin, adonixanthin, and astaxanthin. A method for producing canthaxanthin by culturing the above bacterium, and then collecting carotenoids from bacterial cells or a culture solution after the culturing.

5 Claims, 4 Drawing Sheets

MICROORGANISM AND METHOD FOR PRODUCING CAROTENOID USING IT

TECHNICAL FIELD

The present invention relates to a novel microorganism and a method for producing carotenoids, in particular, canthaxanthin using the same.

BACKGROUND ART

Carotenoids, such as astaxanthin, zeaxanthin, phoenicoxanthin, canthaxanthin, adonixanthin, and β-carotene, have been used as a naturally occurring pigment which is added to food, medicine, quasi-drugs, cosmetics and the like. In addition, because of their antioxidant properties, the carotenoids have also been widely used as an antioxidant substance. The carotenoids described above are widely distributed in plants, animals, and microorganisms, and several hundred types of natural carotenoids have already been identified (for example, see Non-Patent Document 1).

As microorganisms which synthesize functional carotenoids, a bacterium belonging to the genus *Agrobacterium* (which was later reclassified into the genus *Paracoccus*) was reported by Yokoyama et al (for example, see Non-Patent Document 2). The above bacterium is characterized by synthesizing astaxanthin, which is one of the functional carotenoids, at a high concentration. In addition, a biosynthetic pathway of astaxanthin by the above bacterium was investigated, and a detailed gene-level mechanism was reported (for example, see Non-Patent Document 3). According to the reported biosynthetic pathway, for the synthesis of carotenoids, mevalonic acid, which is a primary metabolite and which is used as a starting material, is processed through a metabolic synthetic pathway of isoprenoid biosynthesis to produce farnesyl pyrophosphate (FPP) having 15 carbon atoms, and the farnesyl pyrophosphate thus formed is then condensed with isopentenyl pyrophosphate (IPP) having 5 carbon atoms, so that geranylgeranyl pyrophosphate (GGPP) having 20 carbon atoms is synthesized. Next, two geranylgeranyl pyrophosphate molecules are condensed with each other, so that phytoene is synthesized. Phytoene is converted into lycopene by a series of desaturation reactions, and this lycopene is further processed by a ring-forming reaction, so that β-carotene is synthesized. Next, when β-carotene is oxidized by a ketonization reaction, canthaxanthin is produced, and when β-carotene is hydroxylated, zeaxanthin is produced. Furthermore, when oxidation reaction is further advanced by ketonization and hydroxylation, astaxanthin is synthesized. The carotenoid biosynthetic pathway described above is shown in FIG. 1.

In addition, it was also reported that some microorganism has no gene encoding the afore-mentioned enzyme which performs ketonization of β-carotene, and hence it selectively synthesizes zeaxanthin (for example, see Non-Patent Document 4). When the same scheme as described above can be applied to the case of canthaxanthin, that is, if a microorganism which has no gene encoding a β-carotene hydroxylase is present, canthaxanthin can be selectively synthesized; however, separation of a novel microorganism that selectively synthesizes canthaxanthin has not be reported as of today.

Canthaxanthin is an effective substance as a functional carotenoid to revive the colors of farm-raised fish, hen eggs, and the like; however, canthaxanthin is obtained from a carotenoid extract by purification and is then simply used. Since the carotenoid extract contains many carotenoids having chemical properties similar to those of canthaxanthin, extraction and purification thereof have not been easily performed (for example, see Patent Documents 1 and 2). Accordingly, a substance, such as microorganism, which accumulates canthaxanthin at a high concentration, has been desired.

[Patent Document 1] Japanese Unexamined Patent Application Publication No. 6-237787

[Patent Document 2] Japanese Unexamined Patent Application Publication No. 2003-304875

[Non-Patent Document 1] Eric A. Johnson et al., Microbial carotenoids, Advances in Biochemical Engineering, Vol 53, pp. 119 to 178 (1995).

[Non-Patent Document 2] A Yokoyama et al., Production of astaxanthin and 4-ketozeaxanthin by marine bacterium, *Agrobacterium aurantiacum*, Biosci. Biotechnol. Biochem., 58: 1842 to 1844 (1994).

[Non-Patent Document 3] N. Misawa et al., Structure and functional analysis of a marine bacterial carotenoid biosynthesis gene cluster and astaxanthin biosynthetic pathway proposed at the gene level, J. Bacteriology, 177: 6575 to 6584 (1995).

[Non-Patent Document 4] L. Pasamontes et al., Isolation and characterization of carotenoid biosynthesis genes of *Flavobacterium* sp. strain R1534, GENE, 185: 35 to 41 (1997).

DISCLOSURE OF THE INVENTION

Problems to be Solved by the Invention

An object of the present invention is to provide a canthaxanthin-selective-synthesis bacterium which can easily extract and purify canthaxanthin that is one of carotenoids. In addition, the present invention also has an object to provide a method for producing canthaxanthin by a culture method.

Means for Solving the Problems

Through intensive research carried out by the inventors of the present invention in order to achieve the objects described above, it was discovered that when mutation is introduced into a bacterium belonging to the genus *Paracoccus* which produces carotenoids, canthaxanthin is selectively synthesized, and as a result, the present invention was made. That is, the present invention relates to a bacterium belonging to the genus *Paracoccus* which selectively synthesizes canthaxanthin, the bacterium being obtained by breeding a bacterium belonging to the genus *Paracoccus* which produces carotenoids. In addition, the present invention relates to a method for producing canthaxanthin in which the afore-mentioned bacterium is cultured, followed by collection of canthaxanthin from bacterial cells and/or a culture solution. That is, the present invention relates to the following.

(1) According to a first aspect of the present invention, there is provided a carotenoid producing bacterium belonging to the genus *Paracoccus*, which selectively produces canthaxanthin.

(2) In the bacterium according to the above (1), the amount of canthaxanthin is not less than 90 percent by weight of the total amount of produced carotenoids including β-carotene, β-cryptoxanthin, echinenone, canthaxanthin, 3-hydroxyechinenone, 3'-hydroxyechinenone, zeaxanthin, phoenicoxanthin, adonixanthin, and astaxanthin.

(3) In accordance with a second aspect of the present invention, there is provided a bacterium capable of selectively synthesizing canthaxanthin, which is produced by introducing mutation into a gene encoding a β-carotene hydroxylase by a mutation treatment of an astaxanthin synthesizing bacterium so as to degrade activity of the β-carotene hydroxylase.

(4) In accordance with a third aspect of the present invention, there is provided a bacterium capable of selectively synthesizing canthaxanthin, which is produced by introducing mutation into a gene encoding a β-carotene hydroxylase by a mutation treatment of an astaxanthin synthesizing bacterium so as to knock out the gene encoding a β-carotene hydroxylase.

(5) In accordance with a fourth aspect of the present invention, there is provided a carotenoid synthesizing bacterium containing not less than 1 percent by weight (in terms of dried weight) of canthaxanthin in a bacterial cell.

(6) The bacterium according to the above (1) is a carotenoid producing bacterial *Paracoccus* sp. strain TSAO538 (deposition number FERM P-20707)(deposited under the terms of the Budapest Treaty at the AIST Tsukuba Central 6, 1-1, Higashi 1-chome, Tsukuba-shi, Ibarki-ken 306-8566, Japan on Jan. 9, 2007 under accession number FERM BP-10755.

(7) In accordance with a fifth aspect of the present invention, there is provided a method for producing a carotenoid, comprising the steps of culturing the bacterium according to one of the above (1) to (6), and then collecting the carotenoid from bacterial cells or a culture solution.

(8) In the method for producing a carotenoid, according to the above (7), the carotenoid includes canthaxanthin.

Advantages

By the method for producing a carotenoid, according to the present invention, canthaxanthin which is effectively used for food and feed can be produced in an industrial scale.

REFERENCE NUMERALS

1: absorbance (▲) at an OD of 660 nm with culture time
2: total carotenoid concentration (●) with culture time
3: concentration (○) of canthaxanthin

BEST MODE FOR CARRYING OUT THE INVENTION

Hereinafter, the present invention will be described in detail.

As a microorganism used in the present invention, any microorganism may be used regardless of a wild strain or a mutant strain as long as it belongs to the genus *Paracoccus* and has ability of synthesizing canthaxanthin, and in addition, either one of a mutant strain which is mutated by a general mutation treatment and a spontaneous mutant strain may also be used. As a wild strain used in the present invention, for example, *Paracoccus* sp. strain N81106 (deposited to International Patent Organism Depositary, deposition number: FERM P-14023) may be mentioned. In the present invention, a microorganism capable of selectively synthesizing canthaxanthin, obtained by introducing mutation into a wild strain or a mutant strain, which synthesizes carotenoids, is more preferable.

Figure 1:
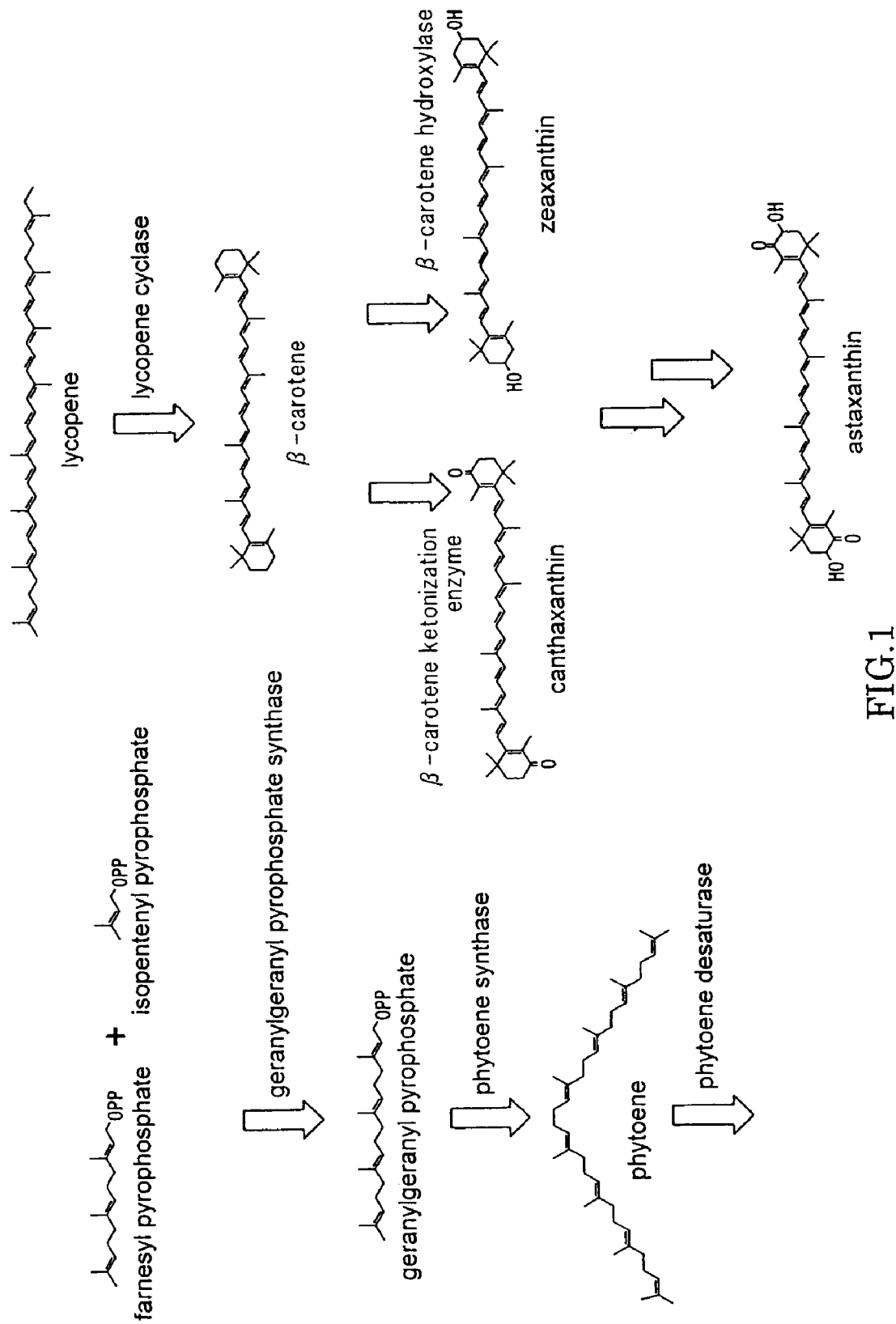
FIG. 1 shows a synthetic pathway for finally producing astaxanthin starting from phytoene via chemical modification of β-carotene.

In the present invention, when mutation is induced into a microorganism having astaxanthin synthesis ability, canthaxanthin synthesis ability can be imparted thereto. As shown in FIG. 1, in a microorganism having astaxanthin synthesis ability, astaxanthin, which is a final product, is synthesized by hydroxylation and ketonization of β-carotene. That is, in order to selectively synthesize canthaxanthin, mutation may be introduced into the crtZ gene, which is a gene encoding a β-carotene hydroxylase, so as to degrade activity of the hydroxylase. Alternately, for example, mutation may be introduced into the crtZ gene, which is a gene encoding a β-carotene hydroxylase, to knock out the gene so as to inhibit the function thereof.

As a bacterium into which mutation is introduced, according to the present invention, a bacterium having resistance against carotenoid metabolic analogue is more preferable, which has high growth ability even when carotenoids are accumulated in cells at a high concentration. As the carotenoid metabolic analogue, for example, α-ionone and β-ionone, which are known to persons skilled in the art, may be mentioned; however, any substance may be used as long as it clears the control of intracellular control mechanism that works when carotenoids are accumulated. In the present invention, "a bacterium having resistance" indicates a bacterium that can grow even when a drug is present at a certain concentration at which the growth of a parent strain is inhibited.

The mutation treatment is a method known to persons skilled in the art in which mutation is accelerated by treatment of cells with a mutagenic substance or UV rays. As a mutagenic substance, for example, a compound, such as N-methyl-N'-nitro-N-nitrosoguanidine or ethyl methane sulfonate, may be mentioned.

In addition, in the present invention, a β-carotene hydroxylase gene may be destroyed or may be knocked out. As a method to destroy or knock out a gene, for example, there may be mentioned a method in which appropriate DNA is inserted into a target gene by a homologous recombination technique, which is one of gene engineering methods known to persons skilled in the art; however, the method is not limited thereto.

In the present invention, after the mutation treatment, a mutant strain is separated, and for evaluation of a desired function, breeding is preferably repeated. In one exemplary method of breeding, bacterial cells of bacterial *Paracoccus* sp. strain TSTT052 (deposited to International Patent Organism Depositary, deposition number: FERM P-20690) that are obtained in advance by culturing are suspended in an aqueous solution of a mutagenic substance and are held for a predetermined period of time, and then the bacterial cells are collected, for example, by centrifugation, so that the mutagenic substance is removed. Subsequently, the cells are cultured on a plate culture medium, followed by selection of colonies of excellent bacterial strains. Colonies with dark color tone are selected and isolated, and the colonies thus isolated are then liquid-cultured. Subsequently, carotenoids are extracted from the bacterial cells, and the amount of the carotenoids thus extracted and the composition thereof are analyzed by HPLC or the like to narrow down bacterial strains having improved productivity, whereby excellent bacterial strains are obtained.

In the present invention, regardless of a wild strain and a mutant strain, any microorganism may be used as long as it belongs to the genus *Paracoccus* and has ability of synthesizing canthaxanthin, and for example, *Paracoccus* sp. strain TSAO538 (deposition number: FERM P-20707) established by the inventors of the present invention may be mentioned.

This bacterial strain has the following mycological properties. In the following properties, + indicates positive, and – indicates negative.

| (a) | Cell shape | Short rod | 0.7 to 0.8 × 1.0 to 1.2 μm |
|---|---|---|---|
| (b) | Spore | – | |
| (c) | Motility | – | |
| (d) | Colony morphology | | |

1) Culture medium: culture medium having a composition shown in Table 1
2) Diameter: 1.0 mm
3) Color: orange
4) Elevation state: lens shape
5) Shape: circular
6) Margin: entire margin
7) Surface profile: smooth
8) Transparency: opaque
9) Degree of viscosity: butter-like (e) Physiological Properties

| 1) | Catalase | + |
|---|---|---|
| 2) | Oxidase | – |
| 3) | Acid/gas generation from glucose | –/– |
| 4) | O/F test for glucose | –/– |

(f) Substrate Assimilation

| 1) | Methanol | – |
|---|---|---|
| 2) | Ethanol | – |
| 3) | Butanol | + |
| 4) | Methylamine | – |
| 5) | Glycerol | – |
| 6) | Glucose | + |
| 7) | Fructose | + |
| 8) | Galactose | + |
| 9) | Ribose | – |
| 10) | Maltose | + |
| 11) | Sucrose | + |
| 12) | Lactose | – |
| 13) | Mannitol | + |
| 14) | Inositol | – |
| 15) | Xylose | – |
| 16) | Mannose | – |
| 17) | Sorbitol | + |
| 18) | Arabinose | – |
| 19) | Trehalose | + |
| 20) | Gluconic acid | – |
| 21) | Acetic acid | – |
| 22) | Lactic acid | + |
| 23) | Citric acid | – |
| 24) | Succinic acid | +W |
| 25) | Malonic acid | +W |
| 26) | Pyruvic acid | +W |
| 27) | Trimethyl-N-oxide | – |
| 28) | Thiosulfuric acid | – |

In the present invention, "selective synthetic ability" indicates the state in which canthaxanthin may be synthesized by a microorganism which synthesizes carotenoids so that canthaxanthin is easily separated and purified. In addition, it is more preferable that the amount of canthaxanthin be not less than 90 percent by weight of the total amount of produced carotenoids including β-carotene, β-cryptoxanthin, echinenone, canthaxanthin, 3-hydroxyechinenone, 3'-hydroxyechinenone, zeaxanthin, phoenicoxanthin, adonixanthin, and astaxanthin. In the case described above, besides β-carotene, β-cryptoxanthin, echinenone, canthaxanthin, 3-hydroxyechinenone, 3'-hydroxyechinenone, zeaxanthin, phoenicoxanthin, adonixanthin, and astaxanthin, the carotenoids further include other carotenoids accumulated in microorganisms.

In the present invention, an excellent bacterial strain may be determined by evaluating an appropriate bacterial strain. When a solid culture medium is used, evaluation may be achieved by picking up an arbitrary colony and subjecting it to liquid culture, followed by evaluation of growth ability and productivity of carotenoids.

Microorganisms used in the methods of the present invention may be cultured in any nutrient culture media well known in the art. As a culture medium used in the present invention, any culture media may be used as long as the bacterium is able to grow and produce carotenoids therein. There can be used molasses, glucose, fructose, maltose, sucrose, starch, lactose, glycerol, acetic acid, and the like as a carbon source; as a nitrogen source, natural ingredients such as corn steep liquor, peptone, yeast extract, meat extract and soybean cake, ammonium salts such as ammonium acetate, ammonium chloride and ammonium sulfate, amino acids such as glutamic acid, aspartic acid, and glycine; as an inorganic salt, sodium chloride and phosphate salts such as sodium primary phosphate, sodium secondary phosphate, potassium primary phosphate, and potassium secondary phosphate; as a metallic ion, magnesium chloride, magnesium sulfate, ferrous sulfate, ferric sulfate, ferrous chloride, ferric chloride, iron citrate, ammonium iron sulfate, calcium chloride dihydrate, calcium sulfate, zinc sulfate, zinc chloride, copper sulfate, copper chloride, manganese sulfate, manganese chloride, and the like; and as vitamins, yeast extract, biotin, nicotinic acid, thiamine, riboflavin, inositol, pyridoxine, and the like.

Bacterial strains used in a culture process may be transferred by a known method from a streak culture plate to a fermentation container. As a preferable method, for example, a method using an agar plate medium, a slant agar medium, or a flask culture solution may be mentioned.

As for a culture condition of a novel microorganism according to the present invention under which carotenoids such as canthaxanthin are produced, any common methods may be used. In a preferred embodiment of the method according to the present invention, culture is preferably executed in a culture solution. For this liquid culture, conditions that are usually used for liquid culture may be used. It is preferable that fermentation be performed for 20 to 200 hours at a culture temperature of 10 to 35° C. and a pH of a culture medium of 6 to 9. As for the culture temperature, the temperature may be changed at an initial stage, a middle stage, and a final stage of culture. As suitable conditions using the nutrient culture medium of the present invention, the culture temperature is 20 to 27° C., the pH is approximately 7.0, and the culture time is 50 to 150 hours.

The pH of the culture medium is controlled in the range of 6.5 to 8.0 and is preferably set to approximately 7.0. For the control of the pH, an aqueous sodium hydroxide, potassium hydroxide, or ammonium solution may be used; however, other substances may also be used.

An analysis method of carotenoids in the present invention is not particularly limited as long as it can efficiently collect carotenoids from bacterial cells or a culture solution, and as an extracting solvent, for example, methanol, ethanol, isopropyl alcohol, acetone, methyl ethyl ketone, methyl isobutyl ketone, dichloromethane, chloroform, dimethylformamide, and dimethylsulfoxide may be mentioned. The quantities of extracted carotenoids are preferably determined by high-performance liquid chromatography which can separate individual carotenoids and which excels in determining the quantity.

For collecting carotenoids and/or canthaxanthin from bacterial cells or a culture solution after culturing, for example, bacterial cells may be separated from a culture solution by centrifugal separation or the like, followed by extraction from both of them using an appropriate organic solvent. As the organic solvent, for example, methanol, ethanol, isopropyl alcohol, acetone, methyl ethyl ketone, methyl isobutyl ketone, dichloromethane, chloroform, dimethylformamide and dimethylsulfoxide. Among the above solvents, acetone may be preferably mentioned. Furthermore, separation and purification may be performed, for example, by liquid chromatography in order to improve the purity. As a separation principle of the liquid chromatography, for example, ion exchange, hydrophobic interaction, and molecular sieve may be mentioned. Reverse-phase chromatography or normal-phase chromatography is preferably used. Alternatively, extraction from cells may be conducted by supercritical fluid extraction.

Alternatively, after completion of culturing, bacterial cells may be separated from a culture medium, for example, by centrifugal separation, decantation, or filtration. The obtained bacterial cells are added with water to form a slurry having a viscosity to be easily handled. In order to prevent decomposition of carotenoids such as canthaxanthin, an appropriate additive may be added to the slurry. As the additive, for example, an antioxidant, such as ascorbic acid, may be mentioned; however, the additive is not limited thereto. Subsequently, the slurry thus prepared is homogenized by a high-pressure homogenizer or a grinder using glass beads or zirconia beads, followed by drying for the use. A preferable drying method is a spray drying method.

The bacterial cells may be directly added to feed for farm-raised fish or the like. Alternatively, as described above, extraction may be performed for the bacterial cells using a polar organic solvent or the like for the use. Cell bodies remaining after the extraction of carotenoids such as canthaxanthin and containing substantially no pigments can be used as ideal supply sources of proteins and vitamins in poultry raising.

EXAMPLES

Hereinafter, the present invention will be described in detail with reference to examples; however, it is to be understood that the present invention is not limited to the examples.

Example 1

Mutagenesis into *Paracoccus* Sp. Strain and Plate Evaluation of Mutant Strain

Bacterial *Paracoccus* sp. strain TSTT052 (deposition number: FERM P-20690) was inoculated into 5 mL of a liquid culture medium shown in Table 1 and was cultured in a tube for 1 day at 25° C. under shaking at 150 rpm. Subsequently, 1 mL of this culture solution was transferred to a 1.5-mL Eppendorf tube and was then centrifuged at 15,000 rpm for 10 minutes to collect bacterial cells. These bacterial cells were suspended in 1 mL of a potassium phosphate buffer solution (buffer solution A) at a concentration of 0.1 M and at a pH of 7.0, were then added with 10 µL of an aqueous solution of N-methyl-N'-nitro-N-nitorosoguanidine (hereinafter referred to as "NTG") at a concentration of 3 mg/mL, and were subsequently held for 30 to 60 minutes. After centrifugal separation was performed to remove a supernatant, the bacterial cells were again suspended in the buffer solution A twice to remove NTG. Furthermore, the bacterial cells were suspended in 0.5 mL of the buffer solution A, were then inoculated into 3 mL of the culture medium shown in Table 1, and were subsequently cultured for 4 to 5 hours. An appropriate amount of the culture solution thus obtained was spread over a plate culture medium which was obtained by addition of agar to a culture medium having the composition shown in Table 1, followed by solidification. Subsequently, culture was performed for 5 days at 25° C. Colonies could be confirmed with the naked eye three days after the start of culture, and the intensity of red color of the colonies could also be discriminated.

Example 2

Culturing of Mutant Strain of Bacterium *Paracoccus* Sp. Strain

Figure 2:
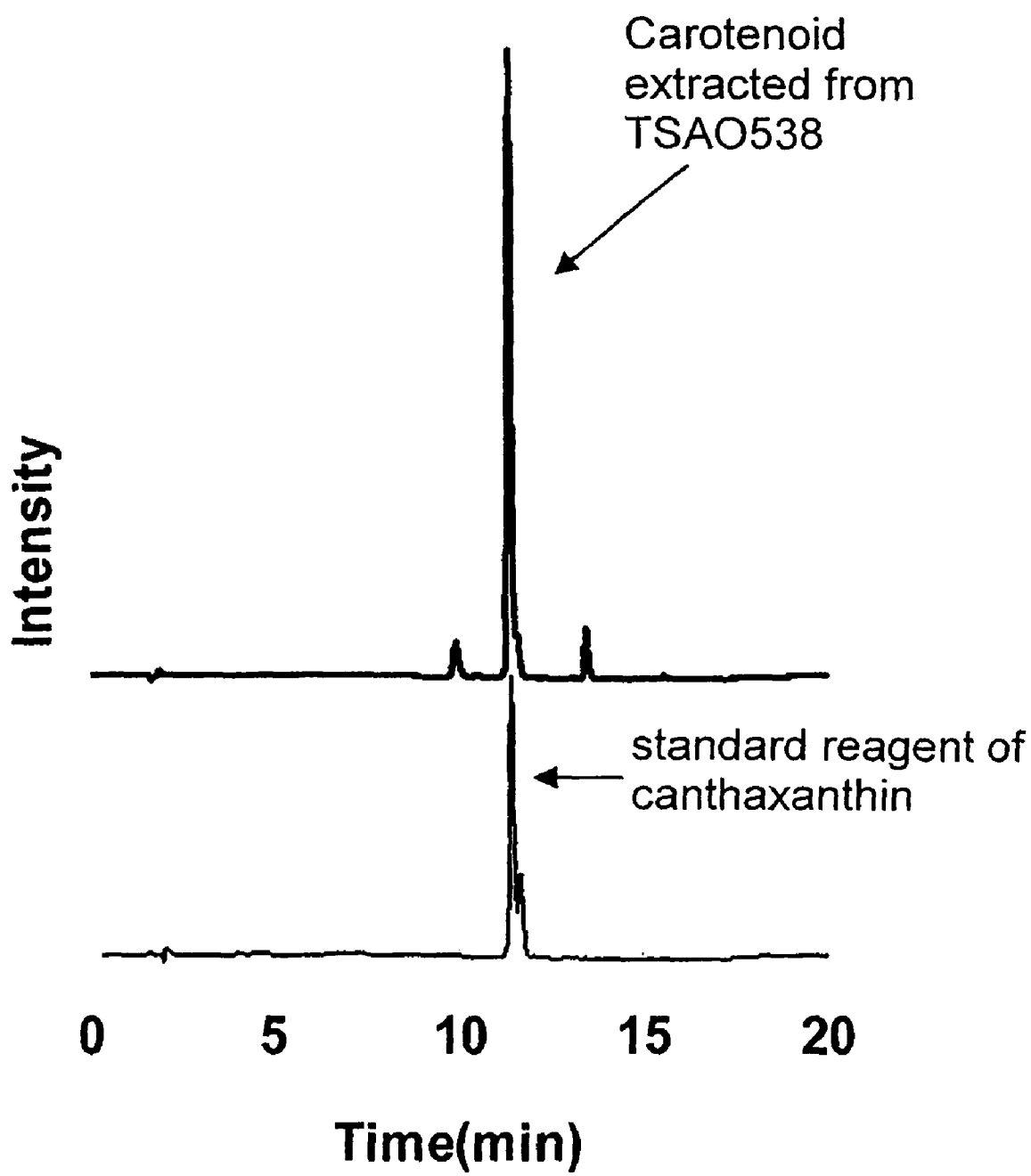
FIG. 2 shows an HPLC chart of carotenoids extracted from strain TSAO538, in which the x axis (horizontal axis) indicates a retention time (unit: minutes), and the y axis (vertical axis) indicates HPLC peak intensity (unit: mV, (arbitrary intensity)).

The bacterial strain obtained in Example 1 was randomly selected, was then inoculated into 5 mL of the culture solution shown in Table 1, and subsequently, was cultured for 1 day at 25° C. Then, 60 mL of a culture medium having the composition shown in Table 1 was sterilized in a 100-mL Erlenmeyer flask equipped with a baffle and was inoculated with 2 mL of the culture solution which was cultured beforehand as described above. After culture was performed for 7 days at 25° C. under shaking (100 rpm), the culture solution was appropriately sampled, and the turbidity (OD 660 nm) and the carotenoid amount were determined. The carotenoid amount was determined by the following process. First, 1 mL of the culture solution was received in a 1.5-mL Eppendorf tube, followed by centrifugal separation at 15,000 rpm for 5 minutes, so that pellets of bacterial cells were obtained. The bacterial cells were then suspended in 20 µL of pure water, and were then added with 200 µl of dimethylformamide and 500 µL of acetone, followed by shaking, so that carotenoids were extracted. After the extraction liquid was processed by centrifugal separation at 15,000 rpm for 5 minutes to remove a residue, the amounts of individual carotenoids were determined by high performance liquid chromatography (hereinafter referred to as "HPLC") using TSK gel-ODS80TM column (manufactured by TOSOH CORPORATION). Separation of carotenoids was executed in the following manner. A mixed solvent of pure water and methyl alcohol as solution A at a mixing ratio of 5 to 95 and a mixed solvent of methyl alcohol and tetrahydrofuran as solution B at a mixing ratio of 7 to 3 were prepared. Subsequently, after the solution A was allowed to pass through the column for 5 minutes at a flow rate of 1 mL/min, the solution A and the solution B were allowed to pass therethrough for 5 minutes at the same flow rate as that described above so as to replace the solution A with the solution B with a linear concentration gradient, and the solution B was then allowed to pass through the column for 5 minutes. The concentration of canthaxanthin was determined by the steps of monitoring an absorbance at 470 nm, and calculating the concentration with reference to a calibration curve prepared beforehand using a standard reagent of canthaxanthin having a known concentration. Among the mutant strains thus evaluated, as a novel mutant strain in which canthaxanthin selective synthesis was confirmed, strain TSAO538 (which was a bacterial strain deposited to International Patent Organism Depositary, deposition number: FERM P-20707) was separated. Canthaxanthin was identified by a retention time of the standard reagent measured by HPLC. FIG. 2 shows a HPLC pattern of a carotenoid extracted from the strain TSAO538, and that of the standard reagent. As shown in FIG. 2, the peak of the carotenoid extracted from the strain TSAO538 coincides with the peak of the standard reagent, and hence, it was confirmed that the strain TSAO538 can selectively synthesize canthaxanthin.

Figure 3:
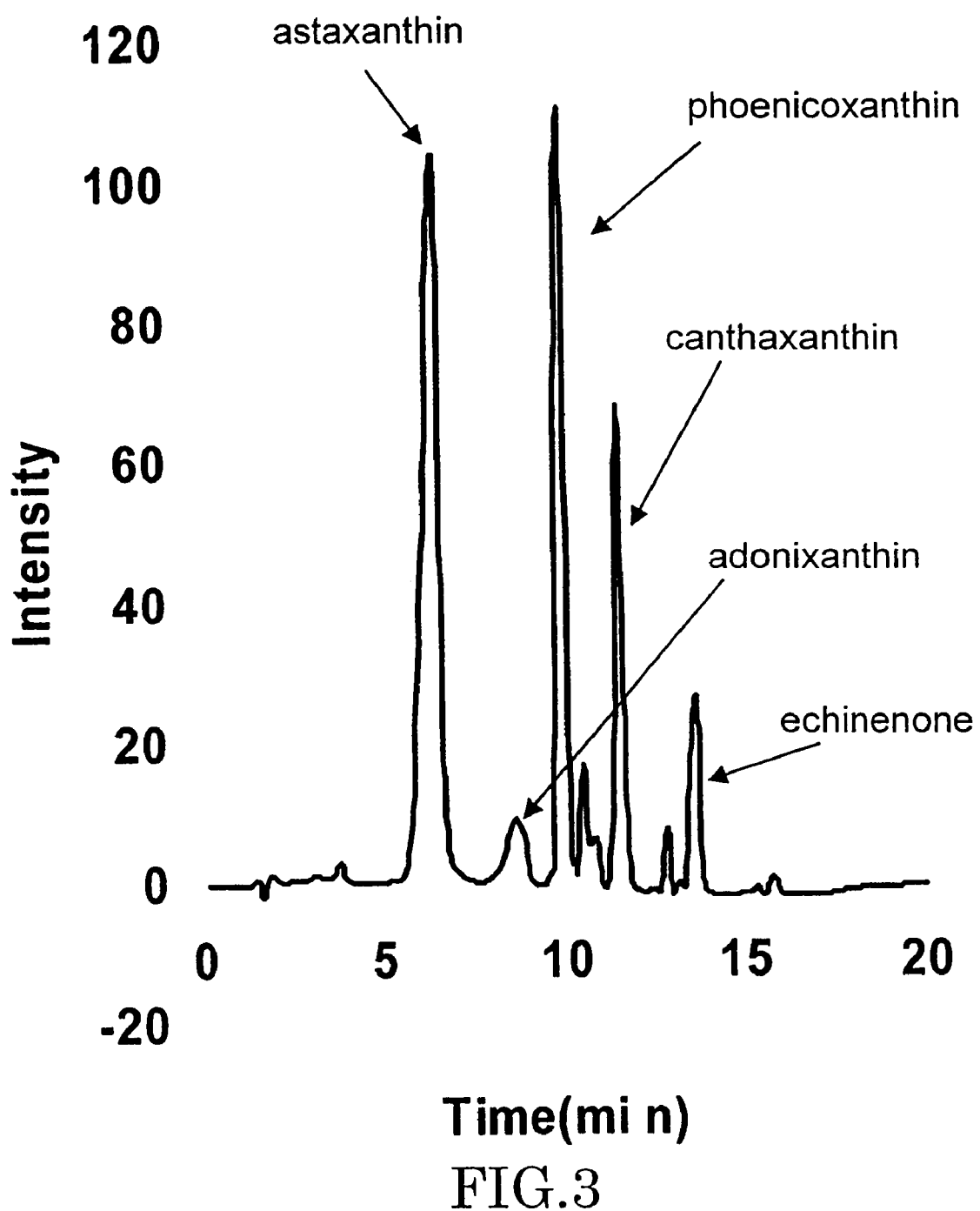
FIG. 3 shows an HPLC chart of carotenoids extracted from strain TSTT052, in which the x axis (horizontal axis) indicates a retention time (unit: minutes), and the y axis (vertical axis) indicates HPLC peak intensity (unit: mV, (arbitrary intensity)).

FIG. 3 shows patterns of carotenoids produced from the strain TSTT052, a strain prior to the mutagenesis, which was cultured in the same manner as described above, the patterns being obtained four days after the start of culture. As shown in FIGS. 2 and 3, the strain TSAO538 selectively synthesizes canthaxanthin differently from the strain TSTT052, and the ratio of canthaxanthin to the carotenoids is more than 90%. The selective synthetic ratio was obtained by the steps of obtaining the production amounts of astaxanthin, zeaxanthin, canthaxanthin, β-carotene, phoenicoxanthin, adonixanthin, and echinenone, and then calculating the ratio of canthaxanthin to the total of the above carotenoids. The results are shown in Table 2.

Figure 4:
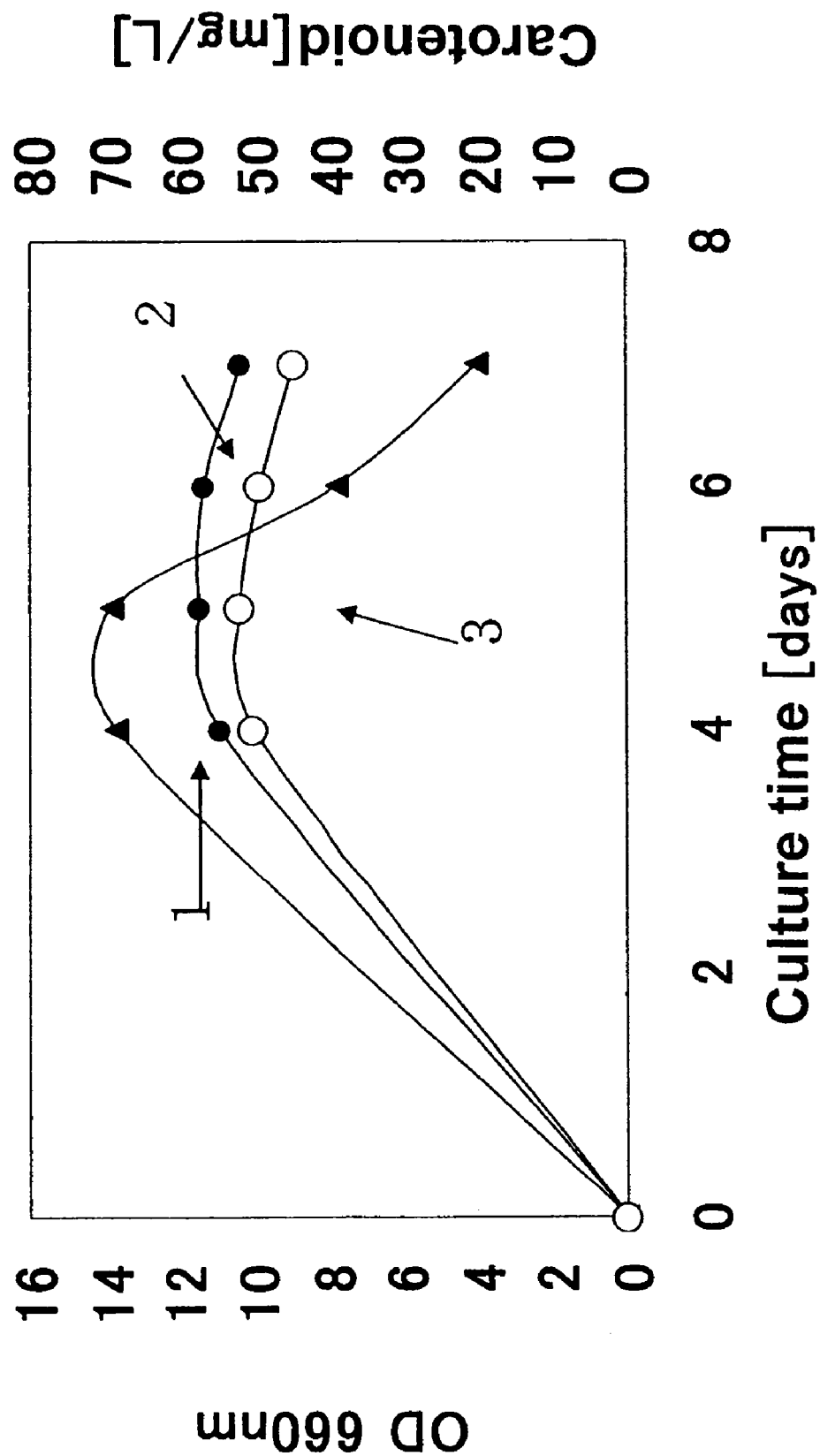
FIG. 4 is a graph showing a culture process of the strain TSAO538, in which the x axis (horizontal axis) indicates a culture time (unit: days), the y axis (left-side vertical axis) indicates absorbance at an OD of 660 nm, and the y axis (right-side vertical axis) indicates the concentration of carotenoid (unit: mg/L).

FIG. 4 is a graph showing the canthaxanthin synthesis by the strain TSAO538 with time. As shown in FIG. 4, with time of culturing the strain TSAO538, canthaxanthin is synthesized, and canthaxanthin is accumulated in cells even 5 days after the start of culture without being decomposed. The content of canthaxanthin per bacterial cell 4 days after the start of culture was approximately 1.2 percent by weight. The weight percent was calculated by obtaining the weight of dried bacterial cells.

TABLE 1

| Components | Addition amount |
| --- | --- |
| Potassium secondary phosphate | 3.6 g/L |
| Potassium primary phosphate | 1.4 g/L |
| Sodium chloride | 8.8 g/L |
| Magnesium sulfate heptahydrate | 0.73 g/L |
| Trypticase peptone | 2 g/L |
| Yeast extract | 1 g/L |
| Glucose | 10 g/L |

TABLE 1-continued

| Components | Addition amount |
| --- | --- |
| Calcium chloride dihydrate | 0.6 mM |
| Ferrous sulfate heptahydrate | 0.1 mM |

TABLE 2

| Carotenoid | Concentration (mg/L) | Ratio (%) |
| --- | --- | --- |
| canthaxanthin | 50.13 | 91.8 |
| astaxanthin | Not more than detection limit | — |
| zeaxanthin | Not more than detection limit | — |
| adonixanthin | Not more than detection limit | — |
| phoenicoxanthin | 2.54 | 4.7 |
| echinenone | 1.91 | 3.4 |
| β-carotene | Not more than detection limit | — |
| Total | | 100 |

INDUSTRIAL APPLICABILITY

Since a novel canthaxanthin selective synthesizing bacterium can easily extract and purify canthaxanthin, which is one of carotenoids, canthaxanthin useful for food and feed can be produced by industrial-scale production.

The invention claimed is:

1. A biologically pure culture of a carotenoid producing bacterium
strain TSAO538, which has been deposited under accession number FERM BP-10755.

2. The bacterium according to claim 1 which produces an amount of canthaxanthin that is not less than 90 percent by weight of the total amount of carotenoids produced including β-carotene, echinenone, canthaxanthin, zeaxanthin, phoenicoxanthin, adonixanthin, and astaxanthin.

3. A method for producing a carotenoid by culturing the bacterial strain as recited in claim 1, comprising: culturing said bacterium of claim 1 in a culture medium under conditions suitable to produce the carotenoid, and then
collecting the carotenoid from bacterial cells or from the culture medium.

4. The method for producing a carotenoid according to claim 3, wherein the carotenoid is canthaxanthin.

5. The method of claim 4, comprising separating canthaxanthin.

* * * * *